United States Patent
Sjöholm

(10) Patent No.: US 6,598,602 B1
(45) Date of Patent: Jul. 29, 2003

(54) MEDICAL NEBULIZER

(75) Inventor: Gösta Sjöholm, Bromma (SE)

(73) Assignee: Siemens-Elema AB, Solna (SE)

( * ) Notice: Subject to any disclaimer, the term of this patent is extended or adjusted under 35 U.S.C. 154(b) by 0 days.

(21) Appl. No.: 09/597,806

(22) Filed: Jun. 19, 2000

(30) Foreign Application Priority Data

Jul. 8, 1999 (SE) .............................................. 9902627

(51) Int. Cl.⁷ .......................... A61M 11/00; B05B 17/06
(52) U.S. Cl. ............................. 128/200.16; 128/200.14; 128/200.18; 128/200.21
(58) Field of Search ................... 128/200.14, 200.16, 128/200.18, 200.19, 200.21, 203.12; 239/338

(56) References Cited

U.S. PATENT DOCUMENTS

| | | | |
|---|---|---|---|
| 3,812,854 A | | 5/1974 | Michaels et al. |
| 5,443,059 A | | 8/1995 | Koch et al. |
| 5,511,726 A | * | 4/1996 | Greenspan et al. ...... 239/102.2 |
| 5,515,842 A | | 5/1996 | Ramseyer et al. |
| 5,743,251 A | * | 4/1998 | Howell et al. ......... 128/200.14 |
| 6,296,196 B1 | * | 10/2001 | Denen et al. .................. 239/4 |

FOREIGN PATENT DOCUMENTS

| | | | |
|---|---|---|---|
| GB | 2272389 | | 5/1994 |
| WO | WO 94/03225 | * | 2/1994 |
| WO | WO 95/01137 | | 1/1995 |
| WO | WO 96/28205 | | 9/1996 |

* cited by examiner

Primary Examiner—Weilun Lo
Assistant Examiner—Darwin P. Erezo
(74) Attorney, Agent, or Firm—Schiff Hardin & Waite

(57) ABSTRACT

A medical nebulizer has a reservoir for medical liquid, a capillary nozzle having a proximal end for receiving liquid from the reservoir and a distal end connectable to an inspiration gas flow path to deliver liquid droplets into an inspiration gas flow, a pump for supplying liquid from the reservoir through the capillary nozzle, and a regulator for regulating the delivery of the liquid to a predetermined amount. The pump supplies the liquid in a continuous flow throughout the delivery of the predetermined amount and a stimulator, such as a piezoelectric vibrator, is provided for vibrating the distal end of the nozzle to stimulate droplet formation.

8 Claims, 4 Drawing Sheets

MEDICAL NEBULIZER

BACKGROUND OF THE INVENTION

1. Field of the Invention

Figure 1:
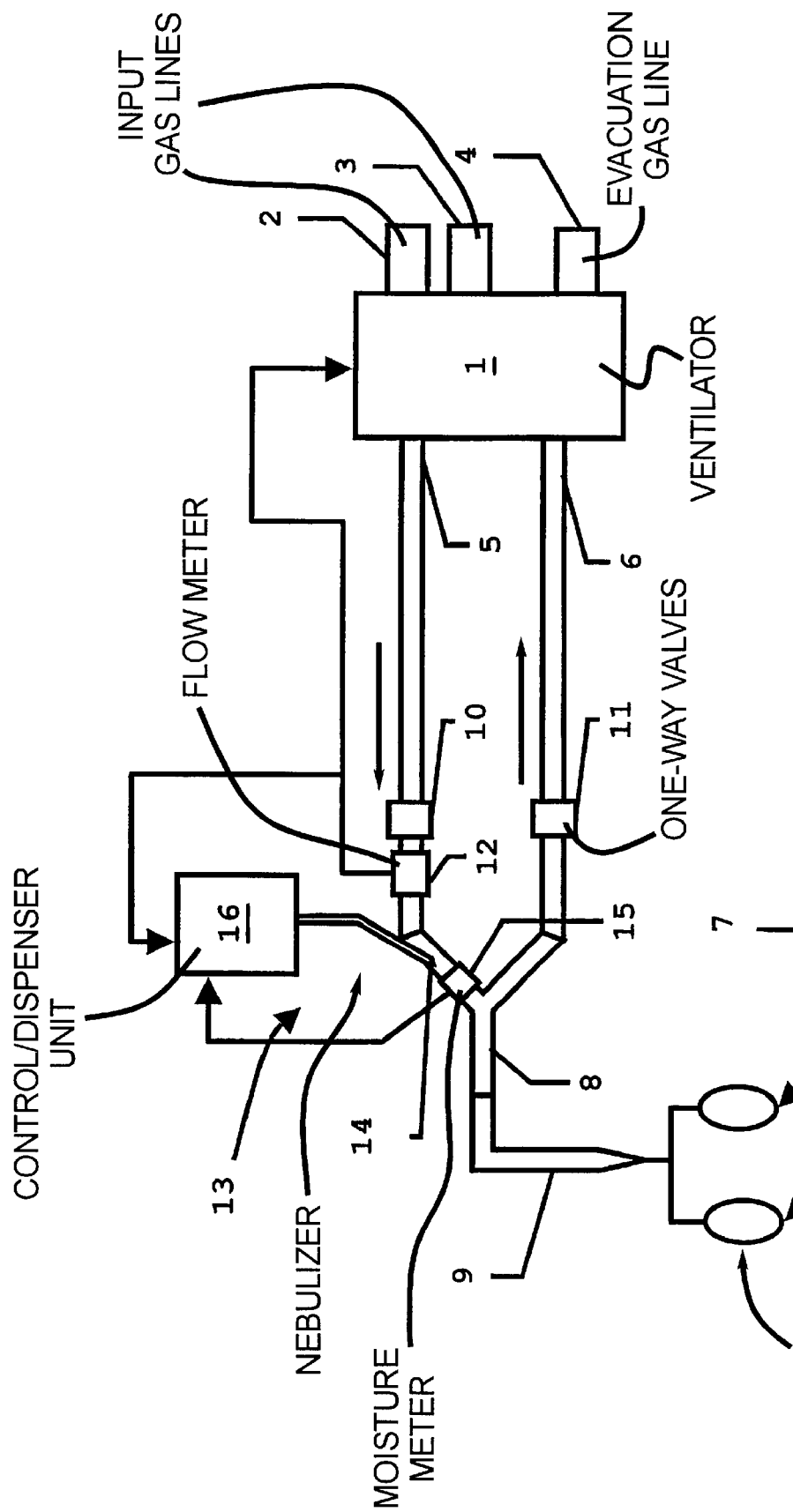

The present invention relates to a medical nebulizer and in particular to a medical nebulizer for providing a nebulized physiologically active liquid into an inspiration gas flow of a mechanical breathing aid.

2. Description of the Prior Art

Medical nebulizers are often used to deliver a metered dose of a physiologically active liquid into an inspiration gas stream for inhalation by a recipient. They generally operate to generate liquid droplets which form an aerosol with the inspiration gas. In other circumstances medical nebulizers may be used to inject water droplets into an inspiration gas stream to provide gas with a suitable moisture content to a recipient, this is particularly useful where the inspiration gas stream is provided by a mechanical breathing aid such as a respirator, ventilator or anaesthetic delivery system.

The term "medical liquid" as used herein means any liquid, regardless of whether it is physiologically active, which is to be supplied to the airways of a recipient.

A known medical nebulizer is described in PCT Application WO 95/01137 and is a hand held device which operates to eject droplets of a medical liquid into a passing air stream (inspiration gas stream) which is generated by a recipient's inhalation through a mouthpiece. This known device has a reservoir for the medical liquid which is connected to a capillary nozzle via a pump which operates directly on liquid within the capillary to eject liquid droplets through the nozzle and into an inspiration gas flow conduit. The pump is a bubble jet or piezoelectric pump, both of which are pulsed to eject a droplet through the nozzle with each pulse. A control unit is also provided to regulate the dose based on the number of pulses provided to the liquid by the pump, for example by regulating the time that a drive signal of known frequency is applied to the piezoelectric element of the pump.

A problem with this device is that the dosage is dependent on the pulse frequency. This limits the device to the delivery of relatively small doses unless a number of nozzle and pump arrangements are employed. This would increase the overall size of the device. Moreover when the piezoelectric pump is used the supply of a pulse to the piezoelectric crystal can stimulate the crystal to produce a pulse train of typically 5 to 6 pulses and lead to an inaccurate dose being provided. Furthermore, the pump is necessarily relatively small as it must act only on liquid within the capillary. The pumping power of such a pump tends to be limited so that at small capillary bore sizes flow resistance can become a problem, limiting the minimum droplet size to typically, microliters.

SUMMARY OF THE INVENTION

An object of the present invention is to provide a medical nebulizer which overcomes the pumping problems associated with the above-described known device.

The above object is achieved in accordance with the principles of the present invention in a medical nebulizer having a reservoir containing a medical liquid and a capillary nozzle having a first end communicating with the reservoir for receiving the medical liquid therefrom, and a second end connectable to an inspiration gas flow path in communication with a patient. A pump supplies the medical liquid from the reservoir through the capillary nozzle in a continuous flow, and a regulator regulates the delivery of the liquid to the nozzle so as to supply a predetermined amount of the medical liquid thereto. A stimulator is mechanically connected to the second end of the capillary nozzle and is operated to vibrate the second end of the capillary nozzle to stimulate droplet formation, so that droplets of the medical liquid are supplied into the inspiration gas flow.

By arranging for the pump to supply a continuous stream of liquid to be nebulized with the aid of a stimulator for vibrating the nozzle a metered dose of medical liquid can be provided in droplet form without the need to monitor the number of droplets.

Moreover, by using a pump which does not act directly on liquid within the capillary a more powerful and less expensive pump, for example a syringe pump, may be used. This enables the capillary bore size to be reduced over known nebulizer and picoliter sized droplets may be supplied. The finer droplet formation allows a more homogeneous vapor to be formed in the inspiration gas stream and a more efficient uptake of the medical agent by the patient.

The reservoir and the nozzle may be releasably couplable. In this way the reservoir may be readily disposed of, replaced or removed for sterilizing as necessary. This also provides an administrative benefit in that an estimate of the amount delivered can be readily obtained from a count of the used reservoir cartridges, enabling for example, stocks to be timely replenished. The pump may be operated continuously and suitable valving provided, such as micro-valves which have particularly well defined cut on and off characteristics, to limit the supply of liquid in order to deliver the predetermined dose from the nebulizer. In this manner inaccuracies in the delivered dose due to the start up and shut down characteristics of the pump can be alleviated.

In order to co-ordinate the delivery of the liquid dose with an inspiration of a recipient, which may be either before, during or after an inspiration, a flow meter can be provided in the flow path of the inspiration gas and adapted to control the delivery dependent on a sensed gas flow.

DESCRIPTION OF THE DRAWINGS

FIG. 1 is a schematic block diagram of a ventilator apparatus having a nebulizer according to the present example.

FIG. 2 is a schematic illustration of a nebulizer according to the present invention usable in the ventilator arrangement of FIG. 1.

FIG. 3 is a schematic illustration of a handheld nebulizer according to the present invention.

FIG. 4 is a schematic illustration of a further embodiment of the nebulizer according to the present invention.

DESCRIPTION OF THE PREFERRED EMBODIMENTS

In FIG. 1 a ventilator apparatus is generally shown in which electronic control signal flow paths are shown by the arrows connecting elements of the apparatus. A conventional ventilator 1 is shown having a number (here two) of input gas lines 2,3 for different gasses and an evacuation gas line 4. Patient breathing conduits 5,6 are provided for transporting breathing gas between the ventilator 1 and lungs 7 of a patient via a Y-piece 8 and endotracheal tube 9. The common branch of the Y-piece 8 is connected to the tube 9 and the separate branches are connected to respective conduits 5,6 in order to provide a flow path 5,8,9 for breathing gas from the ventilator 1 to the patient (inspiration gas flow) which is separate from a flow path 9,8,6 for breathing gas from the patient to the ventilator 1 (expiration gas flow). One-way valves 10,11 are placed in associated conduits 5,6 in order to ensure the correct direction of travel of breathing gas. A flow meter 12 is placed in the inspiration flow path 5,8,9, for example downstream of the one-way valve 10 in the inspiration gas flow direction.

A nebulizer 13 according to the present invention is also provided for supplying water vapor to the inspiration gas flowing to the patients lungs 7 through a capillary nozzle 14 connected to the flow path 5,8,9. The nozzle 14 is disposed to provide the liquid preferably as close to the patient as possible and typically at the Y-piece 8.

A moisture meter 15 is also provided to monitor the moisture content of the inspiration gas after passing the nozzle 14 and to provide an indication of the measured moisture content to a control/dispenser unit 16 of the nebulizer 13 where it is used to control the dosage in combination with gas flow information from the flow meter 12.

Figure 2:
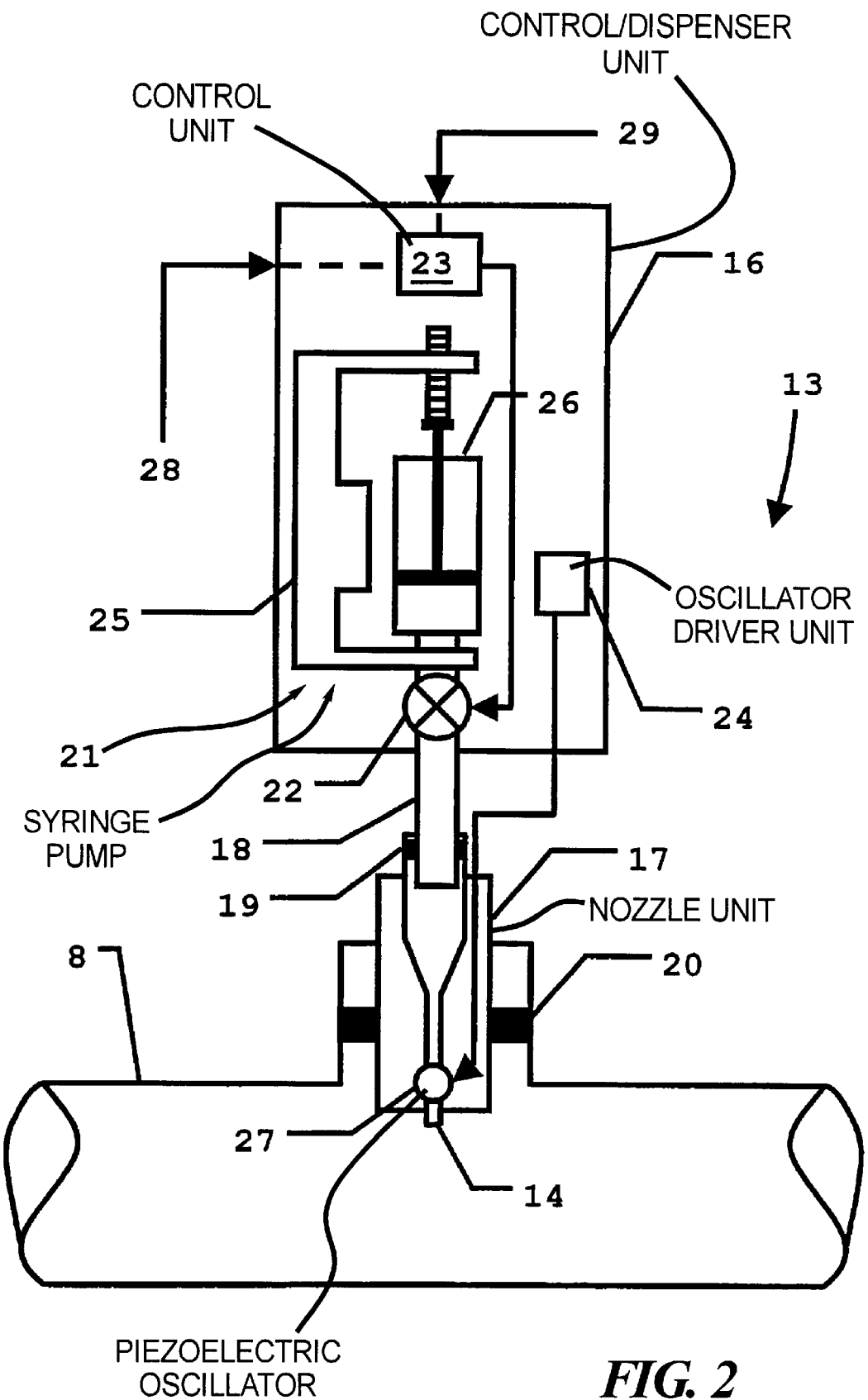
Figure 3:
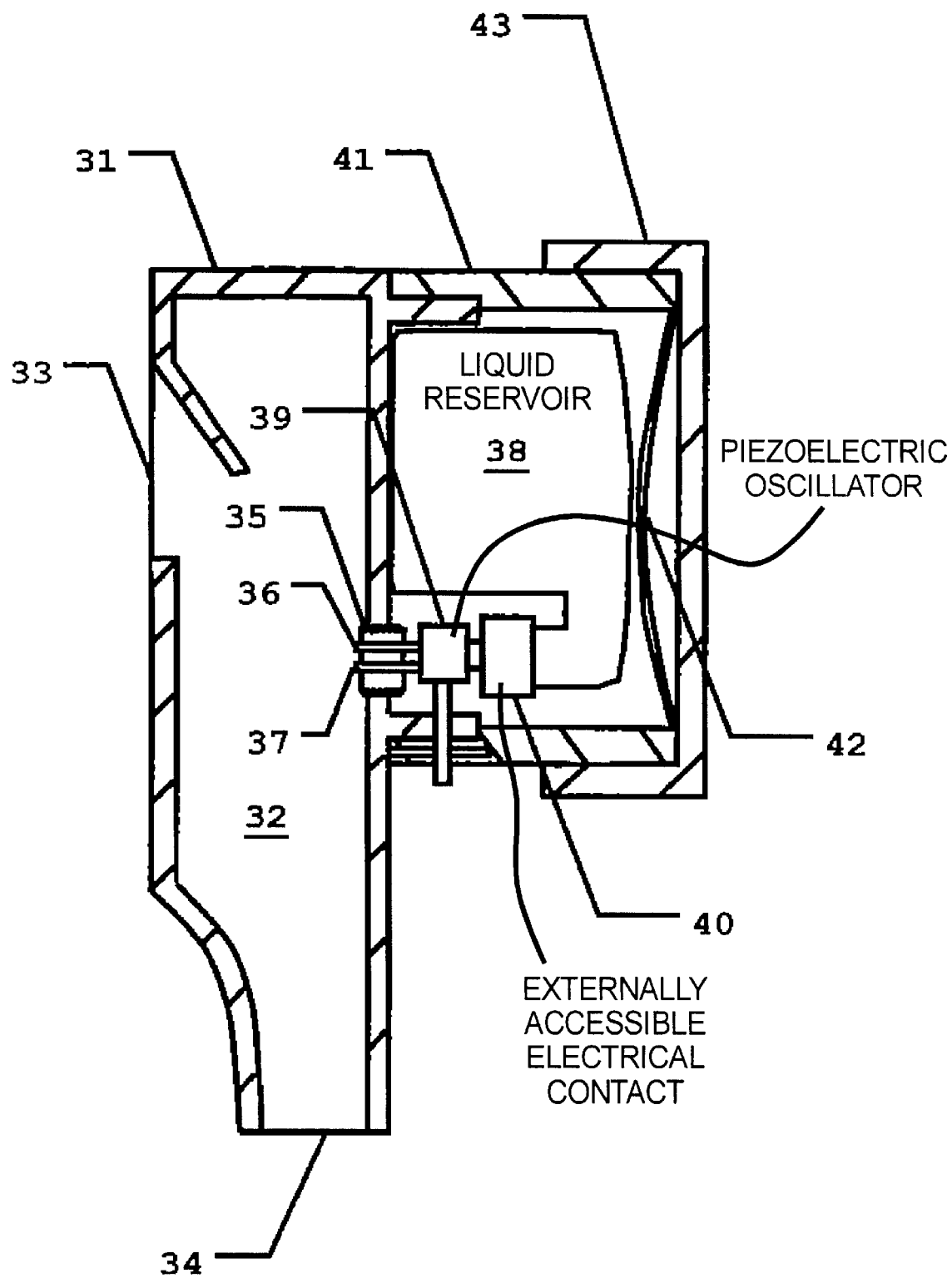
Figure 4:
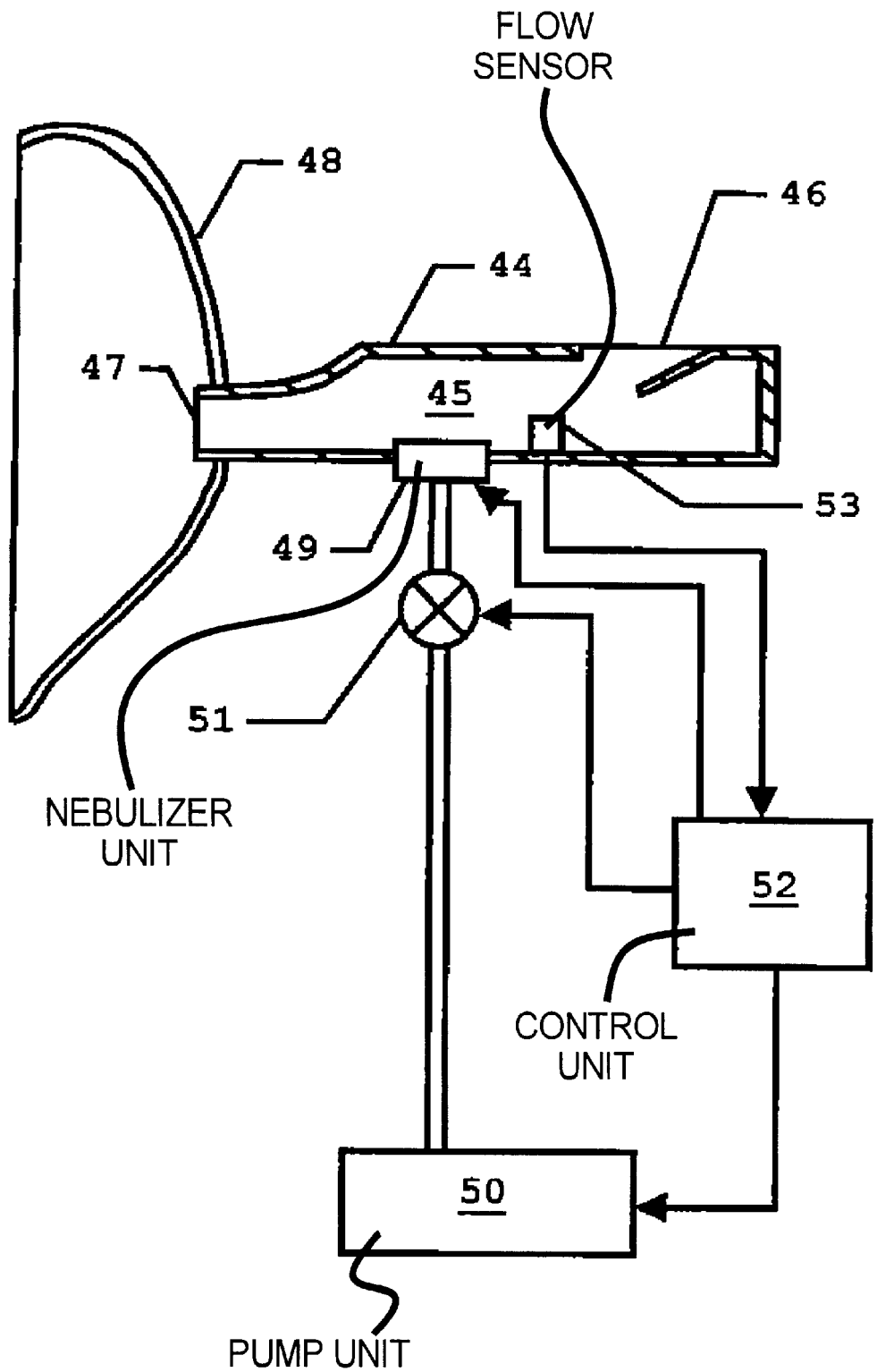

The operation of the nebulizer 13 will be further explained with reference also to FIG. 2. The nebulizer 13 shown in FIG. 2 includes the control/dispenser unit 16 and a nozzle unit 17 which are in fluid communication by means of a conduit 18 which, at one end, is releasably connected to the proximal end of the capillary nozzle 14. This releasable connection may be made using any conventional fluid tight connecting means and is here a press fit connection through an O-ring seal 19. The nozzle unit 17 is also releasably connected to the Y-piece 8 of the ventilator apparatus of FIG. 1, again using a push fit O-ring seal 20. It will be apparent to those skilled in the art that with this arrangement various parts of the nebulizer 13 may be conveniently replaced or removed for cleaning.

The opposite end of the conduit 18 is connected to a syringe pump 21 via a controllable on/off valve 22 which are within the control/dispenser unit 16. Also within this unit 16 is disposed a microprocessor based control unit 23, an oscillator driver unit 24 and a pump power supply 25.

The pump power supply 25 is adapted to continuously pressurize liquid within the syringe reservoir 26 of the syringe pump 21 during the operation of the nebulizer 13 with the dosage being controlled via the on/off valve 22 and the control unit 23.

The oscillator driver unit 24 is also adapted to continuously supply a high frequency (typically in the region of 1 MHZ) drive signal to a piezoelectric oscillator 27 which is disposed within the nozzle unit 17 to vibrate the distal end of the capillary nozzle 14 to stimulate droplet formation in a manner similar to that well known in the art of ink-jet printing. The oscillator unit 24 may be adapted to vary the frequency of the drive signal in dependence of the liquid used, its flow rate and preferred droplet size in order to enhance the operational flexibility of the nebulizer 13 (it is well understood that droplet size depends on, among other things, the liquid flow rate through the nozzle 14, the viscosity of the liquid, and vibrational frequency).

In use, power is provided to the oscillator drive unit 24 and the pump power supply unit 25 from a mains supply via an on/off switch (not shown) accessible externally of the control/dispenser unit 16 and which operate continuously while the nebulizer 13 is switched on. An input signal 28 from the moisture meter 15 of FIG. 1, indicative of the moisture content of inspiration gas, and an input signal 29 from the flow meter 12 of FIG. 1, indicative of the presence and magnitude of an inspiration gas flow, are provided to the control unit 23. The dosage of water from the reservoir 26 necessary to provide the desired relative humidity (which may be user variable or a fixed value) of the inspiration gas is then determined within the control unit 23 and a signal 30 is output to operate the valve 22 to achieve the determined dose. In the present case it is assumed that the flow of water from the syringe pump 21 is predetermined and programmed into the control unit 23. A flow meter (not shown) may be included to directly measure the flow of fluid within the conduit 18, the value of which will be used within the control unit 23 in the regulation of the flow through the valve 22 in order to achieve the determined dose.

In FIG. 3 a nebulizer is shown which is intended for use without a mechanical breathing aid. A mouthpiece 31 defines an inspiration gas conduit 32 having an inlet 33 open to the atmosphere and an outlet 34 intended for insertion into a patient's mouth. A nozzle section 35 is releasably screwed into the mouthpiece 31 so that liquid droplets can pass from distal ends of a number of capillary nozzles (here two) 36,37 into the inspiration gas conduit 32. A piezoelectric oscillator 39, is mechanically coupled to the nozzles 36,37 to vibrate their distal ends and is provided with an externally accessible electrical contact 40 to which oscillator drive signals can be applied. It will be appreciated that the nebulizer of FIG. 3 may be readily modified to include an oscillator drive unit, with or without a battery power supply, to provide a more fully portable nebulizer.

Proximal ends of the nozzles 36,37 are connected to a common liquid reservoir 38 in which is contained a physiologically active liquid. The liquid reservoir 38 is releasably connected to a one-way valve 40, for example using a press fit or screw thread connection for ease of replacement. The valve 40 is arranged to prevent through flow towards the gas conduit 32 until pressure from the liquid exceeds a pre-set amount just above atmospheric. This amount is chosen so that liquid from reservoir 38 cannot flow through the valve 40 under the pressure of its own weight.

The reservoir 38 has a readily deformable container which is housed in a holder 41 having at least one wall section 42 formed of elastically deformable material such that as the section 42 is squeezed the reservoir deforms to expel liquid through the valve 40. A rigid end-cap 43 is provided to push fit over the holder 41. This cap 43 provides physical protection for the elastic wall section 42 against accidental deformation and unintended release of liquid from the reservoir 38. The reservoir 38 may be sized to control the dose provided to the patient so that a single dose will be delivered when the reservoir 38 is fully squeezed.

FIG. 4 shows a nebulizer useful, for example, in the treatment of weak or unconscious patients who are breathing without the aid of a mechanical breathing aid. A common flow section 44 defines a gas conduit 45 having a first aperture 46 open to the atmosphere and a second aperture 47 intended for gas connection to a patient's mouth via a face mask 48. A nebulizer unit 49 is connected to the gas conduit 45 through a wall of the common flow section 44 so that liquid droplets can pass from distal ends of a number of capillary nozzles, which may be vibrated severally or separately using a piezoelectric vibrator within the nebulizer unit 49. The number of nozzles actually used to supply the liquid droplets can be less than the total number of nozzles provided and selected, for example, dependent on a desired rate of supply of nebulized liquid. Moreover, nozzles having a variety of different sizes can be included to further increase the flexibility in supply characteristics of the nebulizer.

A pump unit 50, such as the syringe pump described with respect to FIG. 1, is operably connected to the capillary nozzles of the nebulizer unit 49 via a valve unit 51 and includes a medical liquid reservoir (not shown) from which liquid is pumped through the nozzles of the unit 49 to form a vapor in gas within the conduit 45. A control unit 52, such as a dedicated microprocessor or a suitably programmed personal computer, is also provided to control the operation of the vibrator within the nebulizer unit 49, the valve unit 51 and the pump unit 50 to supply the fluid in dependence of a signal from a flow sensor 53 within the gas conduit 45 of the common flow section 44 indicating a patient's inspiration phase. The control unit 52 can be programmed to operate the pump unit 50 to tend to supply a continuous stream of liquid through the nozzle section 49 and to control the valve unit 51 to open and close and provide a desired amount of medical liquid to the patient. Alternatively, the pump unit 50 can be operated intermittently in order to provide the desired amount of medical liquid. In both alternatives this desired amount can be either pre-set in the control unit 52 employed as a user input, or the control unit 52 can be provided with a user interface.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical nebulizer comprising:

a reservoir containing a medical liquid;

an inspiration gas flow path adapted to deliver inspiration gas to a patient;

a capillary nozzle having a first end communicating with said reservoir for receiving said medical liquid therefrom and an open second end in direct communication with said inspiration gas flow path;

a pump for supplying liquid from said reservoir through said capillary nozzle in a continuous flow;

a regulator for regulating delivery of said medical liquid to said second end of said nozzle in a predetermined amount; and a stimulator in mechanical connection with said second end of said capillary nozzle for vibrating said second end to convert said continuous flow of medical liquid into droplets, said droplets being delivered into said inspiration gas flow directly from said second end of said capillary nozzle.

2. A medical nebulizer as claimed in claim 1 wherein said regulator comprises a valve arrangement operable to limit supply of said medical liquid through said capillary nozzle to said predetermined amount.

3. A medical nebulizer as claimed in claim 1 further comprising a power supply for said pump, and wherein said regulator regulates said power supply to limit the supply of said medical liquid through said capillary nozzle to said predetermined amount.

4. A medical nebulizer as claimed in claim 1 further comprising a flow meter in said inspiration gas flow path which emits a signal dependent on inspiration flow in said inspiration gas flow path, and wherein said regulator is supplied with said signal from said flow meter and regulates the delivery of said medical liquid dependent on said inspiration flow.

5. A medical nebulizer as claimed in claim 1 wherein said pump comprises a syringe pump.

6. A medical nebulizer as claimed in claim 5 wherein said syringe pump contains said reservoir, and wherein said reservoir contained in said syringe pump is releasably couplable to said first end of said capillary nozzle.

7. A medical nebulizer as claimed in claim 1 wherein said inspiration gas flow path comprises an inspiration gas flow path of a mechanical breathing assist apparatus.

8. A medical nebulizer as claimed in claim 1 wherein said capillary nozzle is a first capillary nozzle, and wherein said medical nebulizer further comprises plurality of additional capillary nozzles, each having a first end in communication with said reservoir and a second end in communication with said inspiration gas flow, and each having an individual amount of said medical liquid delivered therethrough in a continuous flow by said pump, the respective individual amounts collectively comprising said predetermined amount, and wherein said stimulator is connected to all of the respective second ends of said capillary nozzle for vibrating all of said second ends to produce droplets which are introduced at said respective second ends into said inspiration gas flow path.

* * * * *